(12) United States Patent
Brown (10) Patent No.: US 11,590,093 B2
(45) Date of Patent: *Feb. 28, 2023

(54) KIT, COMPOSITION, AND COMBINATION THERAPY FOR FRAGILE X SYNDROME

(71) Applicant: Healx Limited, Cambridge (GB)

(72) Inventor: David Brown, Cambridge (GB)

(73) Assignee: HEALX LIMITED

( * ) Notice: Subject to any disclaimer, the term of this patent is extended or adjusted under 35 U.S.C. 154(b) by 0 days.

This patent is subject to a terminal disclaimer.

(21) Appl. No.: 16/383,037

(22) Filed: Apr. 12, 2019

(65) Prior Publication Data

US 2019/0314309 A1   Oct. 17, 2019

Related U.S. Application Data

(60) Provisional application No. 62/657,275, filed on Apr. 13, 2018.

(51) Int. Cl.

| *A61K 31/192* | (2006.01) |
| *A61K 9/00* | (2006.01) |
| *A61K 31/437* | (2006.01) |
| *A61K 31/135* | (2006.01) |
| *A61K 31/353* | (2006.01) |
| *A61K 31/05* | (2006.01) |
| *A61K 31/65* | (2006.01) |
| *A61K 31/35* | (2006.01) |

(52) U.S. Cl.
CPC .......... *A61K 31/192* (2013.01); *A61K 9/0053* (2013.01); *A61K 31/05* (2013.01); *A61K 31/135* (2013.01); *A61K 31/35* (2013.01); *A61K 31/353* (2013.01); *A61K 31/437* (2013.01); *A61K 31/65* (2013.01)

(58) Field of Classification Search
CPC .... A61K 31/192; A61K 9/0053; A61K 31/05; A61K 31/135; A61K 31/35; A61K 31/353; A61K 31/437; A61K 31/65; A61K 31/352; A61K 31/7048; A61K 45/06; A61K 2300/00; A61P 25/00
See application file for complete search history.

(56) References Cited

U.S. PATENT DOCUMENTS

| 4,777,174 A | 10/1988 | Sunshine et al. |
| 10,864,182 B2 | 12/2020 | Brown |
| 2006/0235080 A1 | 10/2006 | Weissbach et al. |
| 2007/0093457 A1 | 4/2007 | Arber et al. |

(Continued)

FOREIGN PATENT DOCUMENTS

| CN | 103622941 A | 3/2014 |
| WO | WO-00/33790 A2 | 6/2000 |

(Continued)

OTHER PUBLICATIONS

Maurin, Fragile X Syndrome: From molecular pathology to therapy, Neuroscience and Biobehavioral Reviews, 2014, 46, pp. 242-255 (Year: 2014).*

(Continued)

*Primary Examiner* — Savitha M Rao
*Assistant Examiner* — Andrew P Lee
(74) *Attorney, Agent, or Firm* — Foley Hoag LLP (57) ABSTRACT

Described herein are kits, compositions, and combination therapies comprising sulindac for use in the treatment of fragile X syndrome (FXS).

11 Claims, 8 Drawing Sheets

(56) References Cited

U.S. PATENT DOCUMENTS

| | | | |
|---|---|---|---|
| 2010/0069331 | A1 | 3/2010 | Weissbach et al. |
| 2015/0141380 | A1 | 5/2015 | Smith et al. |
| 2019/0314308 | A1 | 10/2019 | Brown |

FOREIGN PATENT DOCUMENTS

| | | | | |
|---|---|---|---|---|
| WO | WO-2008/021210 | A2 | 2/2008 | |
| WO | WO-2008133884 | A2 * | 11/2008 | ......... A61K 31/4439 |
| WO | WO-2011/026144 | A1 | 3/2011 | |
| WO | WO-2012/170430 | A1 | 12/2012 | |
| WO | WO-2018/213071 | A1 | 11/2018 | |
| WO | WO-2019/197632 | A1 | 10/2019 | |

OTHER PUBLICATIONS

Dairum, Non-steroidal anti-inflammatory agents, tolmetin and sulindac attenuate quinolinic acid (QA)-induced oxidative stress in primary hippocampal neurons and reduce QA-induced spatial reference memory deficits in male Wistar rats, Life Sciences, 2007, 80, p. 1431-1438 (Year: 2007).*

Bhogal et al., "Fragile X syndrome and model organisms: identifying potential routes of therapeutic intervention," Dis Model Mech, 3(11-12): 693-700 (2010).

Extended European Search Report issued by the European Patent Office in corresponding Application No. EP 18167346.8 dated Aug. 17, 2018.

Farshbaf et al., "Peroxisome proliferator activated receptor gamma (PPAR?) as a therapeutic target for improvement of cognitive performance in Fragile-X," Med Hypotheses, 82(3):291-294 (2014).

Felts et al., "Sulindac Derivatives That Activate the Peroxisome Proliferator-activated Receptor gamma but Lack Cyclooxygenase Inhibition," J Med Chem, 51(16):4911-4919 (2008).

Healx: "Fragile X Syndrome Drug Repurposing Summary Report," Retrieved from the Internet, URL: https://www.fraxa.org/wp-content/uploads/2017/06/Healx-Summary-Report_FRAXA_June-2017.pdf [retrieved on Aug. 3, 2018].

Levin, "Drug Repurposing Study Results Accelerate Progress Towards Fragile X Treatments," Fraxa Research Foundation, Published Oct. 29, 2017. Accessed online Apr. 19, 2018:https://www.fraxa.org/drug-repurposing-accelerates-progress-towards-fragile-x-treatments/.

Zhang et al., "Downregulating the Canonical Wnt/β-catenin Signaling Pathway Attenuates the Susceptibility to Autism-like Phenotypes by Decreasing Oxidative Stress," Neurochem Res, 37(7):1409-1419 (2012).

Huguet et al., "The Genetic Landscapes of Autism Spectrum Disorders," Annual Review of Genomics and Human Genetics, 14: 191-213(2013).

International Search Report for International Application No. PCT/EP2019/059470 dated Aug. 5, 2019.

U.S. Appl. No. 16/383,028, Pending.

Tranfaglia et al., "Repurposing available drugs for neurodevelopmental disorders: the fragile X experience," Neuropharmacol, 147: 74-86 (2018).

Written Opinion of the International Preliminary Examining Authority in Application No. PCT/EP2019/059470 dated Mar. 12, 2020.

Caku et al., "Effect of Lovastatin on Behavior in Children and Adults with Fragile X Syndrome: An Open-Label Study," American Journal of Medical Genetics Part A, 164(11): 2834-2842 (2014).

ChemDrug.com Article., "The phase 2 clinical trial of the new drug ZYN002 for the treatment of fragile X syndrome achieved positive top-line results," retrieved online <https://www.chemdrug.com/news/232/13/60222.html>: 4 pages w/ Machine Translation (Sep. 29, 2017).

Gantois et al., "Metformin ameliorates core deficits in a mouse model of fragile X syndrome," Nature Medicine, 23(6): 674-677 (2017).

Saldarriaga et al., "Fragile X Syndrome," Colombia Medica, 45(4): 190-198 (2014).

* cited by examiner

Figure 3A
Open Field

Figure 3B
Nesting

Figure 3C
Fear Conditioning

Figure 3D
Sociability

Figure 5A
Nesting

Figure 5B
Fear Conditioning

Figure 5C
Sociability

Figure 5D
Sociability

Figure 5E
Open field

Figure 6A
Open Field

Figure 6B
Nesting

Figure 6C
Fear Conditioning

Figure 6D
Sociability

Figure 7A
Open Field

Figure 7B
Nesting

Figure 7C
Fear Conditioning

Figure 7D
Sociability

Figure 8A
Nesting

Figure 8B
Fear Conditioning

Figure 8C
Sociability

Figure 8D
Sociability

Figure 8E
Open Field

KIT, COMPOSITION, AND COMBINATION THERAPY FOR FRAGILE X SYNDROME

CROSS-REFERENCE TO RELATED APPLICATIONS

This application claims the benefit of U.S. Provisional Application No. 62/657,275, filed on Apr. 13, 2018. The entire teachings of the above application is incorporated herein by reference.

FIELD OF THE INVENTION

This invention relates to a kit, composition and combination therapy comprising sulindac for use in the treatment of fragile X syndrome (FXS).

BACKGROUND OF THE INVENTION

Fragile X syndrome, often referred to as fragile X, is the most common inherited cause of intellectual impairment and the most common monogenic cause of autism. It affects around 1 in 4000 males and 1 in 6000 females worldwide. There are a wide range of characteristics associated with fragile X, and typically males are more affected than females. One of the major characteristics associated with fragile x syndrome is intellectual impairment, such as difficulties with cognitive, executive and language performance. Individuals with fragile x syndrome typically have social anxiety characterised by social, emotional and communication difficulties related to extreme shyness, poor eye contact and challenges forming peer relationships. Fragile x syndrome is also associated with hyperactivity and disruptive behaviour, such as short attention span, distractibility, impulsiveness, restlessness, over-activity and sensory problems. Furthermore, individuals with fragile x syndrome often suffer from seizures.

Fragile x syndrome arises from a mutation in a single gene called Fragile X Mental Retardation Gene 1 (FMR1). The 5' UTR of FMR1 contains a CGG trinucleotide repeat that is polymorphic in the population. Once the repeats exceed 200 in number, methylation of the promoter is triggered, and this in turn causes the lack of expression of the gene and translation of its encoded protein, the Fragile X Mental Retardation Protein (FMRP). FMRP is an RNA-binding protein involved in different steps of mRNA metabolism, such as translational control (in soma and dendritic spines) and RNA transport.

At present, there is no effective therapy to treat fragile x syndrome. However, there have been considerable efforts to identify pharmacological targets to treat this disorder. In particular, fragile x syndrome has been a frequent target of repurposing efforts as well as repositioning of drugs in development. Many different standards and methods have been applied to this task. In many cases, repurposing candidates have been identified based primarily on clinical pattern matching, while in others basic disease mechanisms have been studied extensively to identify therapeutic targets, followed by thorough preclinical validation.

Efforts to treat fragile x syndrome have included investigations into; lithium, minocycline, lovastatin, metformin, and EGCG (green tea extract), inter alia. Overall, efforts to treat fragile x syndrome have led to some exciting possibilities, but no definitive successes, despite much effort. This has highlighted the need for new therapies.

Sulindac is a non-steroidal anti-inflammatory drug (NSAID). Sulindac is used in the treatment of acute and chronic inflammatory conditions, such as arthritis, shoulder bursitis and tendonitis, as it exhibits anti-inflammatory, analgesic and antipyretic activities. Like other NSAIDs, the mechanism of action of sulindac is not fully understood. However, it is thought to be related to prostaglandin synthetase inhibition.

Sulindac is a yellow crystalline compound, and is a weak organic acid practically insoluble in water below pH 4.5, but very soluble as the sodium salt or in buffers of pH 6 or higher. Following absorption, sulindac undergoes two major biotransformations (i) reversible reduction to the active sulfide metabolite, and (ii) irreversible oxidation to the inactive sulfone metabolite. Sulindac has the systematic name (Z)-5-fluoro-2-methyl-1-[[p-(methylsulfinyl)phenyl]methylene]-1H-indene-3-acetic acid.

Sulindac is marketed as CLINORIL®, in 200 mg tablets for oral administration. The tablets contain sulindac, cellulose, magnesium stearate, and starch. CLINORIL® is used to treat osteoarthritis, rheumatoid arthritis, ankylosing spondylitis, acute subacromial bursitis/supraspinatus tendinitis and acute gouty arthritis. A typical dosage is 150 mg to 200 mg twice per day.

SUMMARY OF THE INVENTION

The present invention is based on in vivo and in silico data. The below listed compounds have been identified as being useful in the treatment of fragile x syndrome, when used in combination with sulindac. This is based on the below in vivo data, along with in silico data obtained with proprietary algorithms which indicated the compounds listed as Compound A will provide a synergistic combination with sulindac in the treatment of fragile x syndrome.

In a first aspect of the invention, there is provided a kit comprising (i) at least one dose of sulindac, or a pharmaceutically acceptable salt thereof; and (ii) at least one dose of Compound A, or a pharmaceutically acceptable salt thereof, for simultaneous, separate or sequential use in the treatment of fragile x syndrome, wherein Compound A is selected from the following list: minocycline, doxycycline, lovastatin, metformin, epigallo catechin gallate (EGCG—green tea extract), lithium, tideglusib, lamotrigine, acamprosate, ganaxolone, basimglurant, mavoglurant, methylphenidate, L-carnitine, L-acetyl carnitine, zardaverine, ibudilast, metoprolol, penbutolol, fasudil, carbamazepine, midostaurin, sildenafil, tadalafil, gabapentin, stiripentol, donepezil tetracyclines, cannabidiol, curcumin, simvastatin, atorvastatin, pravastatin, fluvastatin, rosuvastatin, pitavastatin, apigenin, telmisartan, medium and long chain fatty acids, indirubin, pregabalin, baclofen, arbaclofen, memantine, ethchlorvynol, fenobam, riluzole, crisaborole, S-rolipram, apremilast, cilomilast, roflumilast, dipyridamole, drotaverine, propentofylline, caffeine, papaverine, trapidil, flavoxate, amlexano X, pentoxifylline, propanolol, pindolol, acebutalol, bisoprolol, carvedilol, labetalol, metipranolol, oxprenalol, pindolol, tertatolol, timolol, topirimate, tianeptine, quercetin, disulfiram, imatinib, gefitinib, selumetinib, refametinib, fusidic acid, sertraline, lorazepam, phenobarbital, vardenafil, udenafil, avanafil, ruxolitinib, momelotinib, bortezomib, carfilzomib, carnosol, riluzole, luteolin, carnosic acid, resveratrol, methylphenidate, menadione, taurine, niacin, clorazepic acid, diazepam and other 'azepam' class drugs, chlordiazepoxide, staurosporin, gaboxadol, progabide, tulrampator, ketamine, decanoic acid, piracetam, pramiracetam, dexmethylphenidate, oglemilast, levetiracetam or vigabatrin.

In a second aspect of the invention, there is provided a kit comprising: (i) at least one dose of sulindac, or a pharmaceutically acceptable salt thereof; and (ii) at least one dose of Compound A, or a pharmaceutically acceptable salt thereof, wherein Compound A is selected from the following list: minocycline, doxycycline, lovastatin, metformin, epigallo catechin gallate (EGCG—green tea extract), lithium, tideglusib, lamotrigine, acamprosate, ganaxolone, basimglurant, mavoglurant, methylphenidate, L-carnitine, L-acetyl carnitine, zardaverine, ibudilast, metoprolol, penbutolol, fasudil, carbamazepine, midostaurin, sildenafil, tadalafil, gabapentin, stiripentol, ganaxolone, donepezil tetracyclines, cannabidiol, curcumin, simvastatin, atorvastatin, pravastatin, fluvastatin, rosuvastatin, pitavastatin, apigenin, telmisartan, medium and long chain fatty acids, indirubin, pregabalin, baclofen, arbaclofen, memantine, ethchlorvynol, fenobam, riluzole, crisaborole, S-rolipram, apremilast, cilomilast, roflumilast, dipyridamole, drotaverine, propentofylline, caffeine, papaverine, trapidil, flavoxate, amlexano X, pentoxifylline, propanolol, pindolol, acebutalol, bisoprolol, carvedilol, labetalol, metipranolol, oxprenalol, pindolol, tertatolol, timolol, topiramate, tianeptine, quercetin, disulfiram, imatinib, gefitinib, selumetinib, refametinib, fusidic acid, sertraline, lorazepam, phenobarbital, vardenafil, udenafil, avanafil, ruxolitinib, momelotinib, bortezomib, carfilzomib, carnosol, riluzole, luteolin, carnosic acid, resveratrol, methylphenidate, menadione, taurine, niacin, clorazepic acid, diazepam and other 'azepam' class drugs, chlordiazepoxide or staurosporin, gaboxadol, progabide, tulrampator, ketamine, decanoic acid, piracetam, pramiracetam, dexmethylphenidate, oglemilast, levetiracetam or vigabatrin.

In a third aspect of the invention, there is provided a composition comprising: (i) at least one dose of sulindac, or a pharmaceutically acceptable salt thereof; and (ii) at least one dose of Compound A, or a pharmaceutically acceptable salt thereof, for use in the treatment of fragile x syndrome, wherein Compound A is selected from the following list: minocycline, doxycycline, lovastatin, metformin, epigallo catechin gallate (EGCG—green tea extract), lithium, tideglusib, lamotrigine, acamprosate, ganaxolone, basimglurant, mavoglurant, methylphenidate, L-carnitine, L-acetyl carnitine, zardaverine, ibudilast, metoprolol, penbutolol, fasudil, carbamazepine, midostaurin, sildenafil, tadalafil, gabapentin, stiripentol, donepezil, tetracyclines, cannabidiol, curcumin, simvastatin, atorvastatin, pravastatin, fluvastatin, rosuvastatin, pitavastatin, apigenin, telmisartan, medium and long chain fatty acids, indirubin, pregabalin, baclofen, arbaclofen, memantine, ethchlorvynol, fenobam, riluzole, crisaborole, S-rolipram, apremilast, cilomilast, roflumilast, dipyridamole, drotaverine, propentofylline, caffeine, papaverine, trapidil, flavoxate, amlexano X, pentoxifylline, propanolol, pindolol, acebutalol, bisoprolol, carvedilol, labetalol, metipranolol, oxprenalol, pindolol, tertatolol, timolol, topiramate, tianeptine, quercetin, disulfiram, imatinib, gefitinib, selumetinib, refametinib, fusidic acid, sertraline, lorazepam, phenobarbital, vardenafil, udenafil, avanafil, ruxolitinib, momelotinib, bortezomib, carfilzomib, carnosol, riluzole, luteolin, carnosic acid, resveratrol, methylphenidate, menadione, taurine, niacin, clorazepic acid, diazepam and other 'azepam' class drugs, chlordiazepoxide staurosporin, gaboxadol, progabide, tulrampator, ketamine, decanoic acid, piracetam, pramiracetam, dexmethylphenidate, oglemilast, levetiracetam or vigabatrin.

In a fourth aspect of the invention, there is provided a composition comprising: (i) at least one dose of sulindac, or a pharmaceutically acceptable salt thereof; and (ii) at least one dose of Compound A, or a pharmaceutically acceptable salt thereof, wherein Compound A is selected from the following list: minocycline, doxycycline, lovastatin, metformin, epigallo catechin gallate (EGCG- green tea extract), lithium, tideglusib, lamotrigine, acamprosate, ganaxolone, basimglurant, mavoglurant, methylphenidate, L-carnitine, L-acetyl carnitine, zardaverine, ibudilast, metoprolol, penbutolol, fasudil, carbamazepine, midostaurin, sildenafil, tadalafil, gabapentin, stiripentol, donepezil, tetracyclines, cannabidiol, curcumin, simvastatin, atorvastatin, pravastatin, fluvastatin, rosuvastatin, pitavastatin, apigenin, telmisartan, medium and long chain fatty acids, indirubin, pregabalin, baclofen, arbaclofen, memantine, ethchlorvynol, fenobam, riluzole, crisaborole, S-rolipram, apremilast, cilomilast, roflumilast, dipyridamole, drotaverine, propentofylline, caffeine, papaverine, trapidil, flavoxate, amlexano X, pentoxifylline, propanolol, pindolol, acebutalol, bisoprolol, carvedilol, labetalol, metipranolol, oxprenalol, pindolol, tertatolol, timolol, topiramate, tianeptine, quercetin, disulfiram, imatinib, gefitinib, selumetinib, refametinib, fusidic acid, sertraline, lorazepam, phenobarbital, vardenafil, udenafil, avanafil, ruxolitinib, momelotinib, bortezomib, carfilzomib, carnosol, riluzole, luteolin, carnosic acid, resveratrol, methylphenidate, menadione, taurine, niacin, clorazepic acid, diazepam and other 'azepam' class drugs, chlordiazepoxide staurosporin, gaboxadol, progabide, tulrampator, ketamine, decanoic acid, piracetam, pramiracetam, dexmethylphenidate, oglemilast, levetiracetam or vigabatrin.

In a fifth aspect of the invention, there is provided a method of treating fragile x syndrome comprising administering the patient simultaneously, separately or sequentially with: (i) at least one dose of sulindac, or a pharmaceutically acceptable salt thereof; and (ii) at least one dose of Compound A, or a pharmaceutically acceptable salt thereof, wherein Compound A is selected from the following list: minocycline, doxycycline, lovastatin, metformin, epigallo catechin gallate (EGCG- green tea extract), lithium, tideglusib, lamotrigine, acamprosate, ganaxolone, basimglurant, mavoglurant, methylphenidate, L-carnitine, L-acetyl carnitine, zardaverine, ibudilast, metoprolol, penbutolol, fasudil, carbamazepine, midostaurin, sildenafil, tadalafil, gabapentin, stiripentol, ganaxolone, donepezil, tetracyclines, cannabidiol, curcumin, simvastatin, atorvastatin, pravastatin, fluvastatin, rosuvastatin, pitavastatin, apigenin, telmisartan, medium and long chain fatty acids, indirubin, pregabalin, baclofen, arbaclofen, memantine, ethchlorvynol, fenobam, riluzole, crisaborole, S-rolipram, apremilast, cilomilast, roflumilast, dipyridamole, drotaverine, propentofylline, caffeine, papaverine, trapidil, flavoxate, amlexano X, pentoxifylline, propanolol, pindolol, acebutalol, bisoprolol, carvedilol, labetalol, metipranolol, oxprenalol, pindolol, tertatolol, timolol, topiramate, tianeptine, quercetin, disulfiram, imatinib, gefitinib, selumetinib, refametinib, fusidic acid, sertraline, lorazepam, phenobarbital, vardenafil, udenafil, avanafil, ruxolitinib, momelotinib, bortezomib, carfilzomib, carnosol, riluzole, luteolin, carnosic acid, resveratrol, methylphenidate, menadione, taurine, niacin, clorazepic acid, diazepam and other 'azepam' class drugs, chlordiazepoxide staurosporin, gaboxadol, progabide, tulrampator, ketamine, decanoic acid, piracetam, pramiracetam, dexmethylphenidate, oglemilast, levetiracetam or vigabatrin.

DETAILED DESCRIPTION

As fragile x is a syndrome, there are a number of different manifestations and symptoms in patients. These include; intellectual impairment, such as difficulties with cognitive, executive and language performance, short-term memory, executive function, visual memory and visual-spatial relationships; autism; social anxiety (i.e. difficulties in social interaction) such as poor eye contact, gaze aversion, prolonged time to commence social interaction, and challenges forming peer relationships; hyperactivity and repetitive behaviour, including very short attention spans, hypersensitivity to visual, auditory, tactile, and olafactory stimuli, distractibility, impulsiveness, restlessness and over-activity; disruptive behaviour, including fluctuating mood, irritability, self-injury and aggression; obsessive compulsive disorder (OCD); ophthalmologic problems, such as strabismus; seizures; difficulties with working memory, which involves the temporary storage of information while processing the same or other information; difficulties with phonological memory (or verbal working memory); and fragile X-related primary ovarian insufficiency (FXPOI).

In the present invention, a kit or a composition comprising sulindac and Compound A is used to treat one or more of the above symptoms, and is therefore an effective treatment of fragile x syndrome. Preferably, the kit or composition according to the present invention is used for treatment of fragile x syndrome when the patient is exhibiting typical symptoms of the syndrome including social anxiety, hyperactivity, memory loss and/or disruptive behaviour. More preferably, the kit or composition according to the present invention is used for the treatment of fragile x syndrome, wherein the patient is exhibiting hyperactivity, memory loss and/or disruptive behaviour.

The term "hyperactivity" has its normal meaning in the art. Hyperactivity may include having very short attention spans, hypersensitivity to visual, auditory, tactile, and olafactory stimuli, distractibility, impulsiveness, restlessness and/or over-activity.

The term "social anxiety" has its normal meaning in the art. It may also be termed as difficulties in social interaction or low sociability. Social anxiety may include having poor eye contact, gaze aversion, prolonged time to commence social interaction, social avoidance or withdrawal and challenges forming peer relationships.

The term "memory loss" has its normal meaning in the art. It refers to an inability to retain information either short-term or long-term. It may also be called memory impairment. It may include difficulties with cognitive, executive and language performance, executive function and visual memory. It may also include difficulties with working memory, also called short-term memory (i.e. the temporary storage of information while processing the same or other information) and difficulties with phonological memory (or verbal working memory).

The term "disruptive behaviour" has its normal meaning in the art. It may also include repetitive behaviour. It may also include fluctuating mood, irritability, self-injury and aggression.

It is known that sulindac undergoes two major biotransformations following absorption (i) reversible reduction to the sulphide metabolite, and (ii) irreversible oxidation to the sulfone metabolite. However, the mechanism by which sulindac treats fragile x syndrome is not yet known. Therefore, for the avoidance of doubt, any reference to sulindac also embraces its metabolites (both the sulphide and sulfone metabolites).

In the present invention, for the kits or compositions according to the invention, Compound A is selected from the following list: minocycline, doxycycline, lovastatin, metformin, epigallocatechin gallate (EGCG-green tea extract), lithium, sertraline, tideglusib, lamotrigine, acamprosate, ganaxolone, basimglurant, mavoglurant, methylphenidate, L-carnitine, L-acetyl carnitine, zardaverine, ibudilast, metoprolol, penbutolol, fasudil, carbamazepine, midostaurin, sildenafil, tadalafil, gabapentin, stiripentol, donepezil, tetracyclines, cannabidiol, curcumin, simvastatin, atorvastatin, pravastatin, fluvastatin, rosuvastatin, pitavastatin, apigenin, telmisartan, medium and long chain fatty acids, indirubin, pregabalin, baclofen, arbaclofen, memantine, ethchlorvynol, fenobam, riluzole, crisaborole, S-rolipram, apremilast, cilomilast, roflumilast, dipyridamole, drotaverine, propentofylline, caffeine, papaverine, trapidil, flavoxate, amlexanox, pentoxifylline, propranolol, pindolol, acebutalol, bisoprolol, carvedilol, labetalol, metipranolol, oxprenalol, pindolol, tertatolol, timolol, topirimate, tianeptine, quercetin, disulfiram, imatinib, gefitinib, selumetinib, refametinib, fusidic acid, lorazepam, phenobarbital, vardenafil, udenafil, avanafil, ruxolitinib, momelotinib, bortezomib, carfilzomib, carnosol, luteolin, carnosic acid, resveratrol, menadione, taurine, niacin, clorazepic acid, diazepam and other 'azepam' class drugs, chlordiazepoxide, staurosporine, gaboxadol, progabide, tulrampator, ketamine, decanoic acid, piracetam, pramiracetam, dexmethylphenidate, oglemilast, levetiracetam and vigabatrin.

In a preferred embodiment, for the kits or compositions according to the present invention, Compound A is selected from the following list: minocycline, doxycycline, lovastatin, metformin, epigallo catechin gallate (EGCG—green tea extract), quercetin, lithium, sertraline, topiramate, cannabidiol, tideglusib, lamotrigine, acamprosate, ganaxolone, basimglurant, mavoglurant, methylphenidate, L-carnitine, L-acetyl carnitine, zardaverine, ibudilast, metoprolol, penbutolol, fasudil, carbamazepine, midostaurin, gabapentin, stiripentol, fenobam, and donepezil.

More preferably, Compound A is selected from minocycline, doxycycline, lovastatin, metformin, quercetin, lithium, sertraline, topiramate, cannabidiol, zardaverine, ibudilast, fasudil, midostaurin, fenobam, metoprolol and donepezil. More preferably, it is selected from ibudilast, sertraline, quercetin, cannabidiol, minocycline, topiramate and metoprolol.

Most preferably, Compound A is selected from ibudilast, sertraline, quercetin, cannabidiol, minocycline and topiramate.

Minocycline is a tetracycline antibiotic which is commonly used in the treatment of acne vulgaris.

Doxycycline is a synthetic, broad-spectrum tetracycline antibiotic exhibiting antimicrobial activity. It is commonly used in the treatment of bacterial pneumonia and acne vulgaris.

Lovastatin is a cholesterol lowering agent isolated from a strain of Aspergillus terreus.

Metformin is a biguanide hypoglycemic agent used in the treatment of non-insulin-dependent diabetes mellitus.

Epigallo catechin gallate (EGCG), also known as epigallocatechin-3-gallate, is the ester of epigallocatechin and gallic acid and is a type of catechin. It is found in high content in green tea.

Sertraline is a selective serotonin re-uptake inhibitor (SSRI) used in the treatment of major depressive disorder.

Lithium medication is commonly used in the treatment of psychiatric disorders.

Quercetin is a plant flavanol found in many fruits, vegetables, and grains. It is used in dietary supplements, beverages and foods. It has anti-oxidant activity and is also known to have non-specific protein kinase enzyme inhibiting properties and other pleiotropic actions.

Topiramate is a sulfamate modified fructose diacetonide used in the treatment of epilepsy.

Cannabidiol is a phytocannabinoid.

Tideglusib is a small molecule non-ATP-competitive glycogen synthase kinase 3 (GSK-3) inhibitor. It is currently being investigated for possible uses in Alzheimer's disease.

Lamotrigine is a synthetic phenyltriazine which is used as an antiseizure medication. It is commonly used to treat epilepsy and bipolar disorder.

Acamprosate is a synthetic amino acid and a neurotransmitter analogue that is used in management of alcohol dependence and abuse.

Ganaxolone is the 3β-methylated synthetic analog of allopregnanolone; it belongs to a class of compounds referred to as neurosteroids. It is currently being investigated for the treatment of epilepsy.

Basimglurant is a mGlu5 negative allosteric modulator currently being investigated for treatment of depression and major depressive disorder.

Mavoglurant is a mGluR5 antagonist.

Methylphenidate is a central nervous system (CNS) stimulant. It is commonly used for the therapy of attention deficit disorder and narcolepsy.

L-carnitine, also called levocarnitine, is an amino acid derivative. It is commonly used to treat carnitine deficiency. L-acetyl carnitine is an acetylated form of L-carnitine.

Zardaverine is a phospho-diesterase 4 inhibitor.

Ibudilast is an anti-inflammatory and neuroprotective agent. It is commonly used in the treatment of asthma and stroke.

Metoprolol is a selective adrenergic beta-1 blocking agent that is commonly used to treat hypertension, angina pectoris and myocardial infarction.

Penbutolol is a nonselective beta-blocker used as an antihypertensive and an antianginal agent.

Fasudil is a Rho kinase inhibitor and vasodilator. It is used to treat cerebral vasospasm.

Carbamazepine is a tricyclic compound which is an anticonvulsant drug. It is commonly used to treat seizures.

Midostaurin is a synthetic indolocarbazole multikinase inhibitor. It is used in the treatment of acute myeloid leukemia and systemic mastocytosis.

Gabapentin is an anticonvulsant that is used in the treatment of epilepsy and neuropathic pain syndromes.

Stiripentol is an anticonvulsant drug used in the treatment of epilepsy.

Fenobam is imidazole derivative.

Donepezil is an oral acetylcholinesterase inhibitor used for therapy of Alzheimer's disease.

In a preferred embodiment, for the kits or compositions according to the present invention, Compound A is selected from the following list: minocycline, doxycycline, lovastatin, metformin, epigallo catechin gallate (EGCG—green tea extract), lithium, tideglusib, lamotrigine, acamprosate, ganaxolone, basimglurant, mavoglurant, methylphenidate, L-carnitine, L-acetyl carnitine, tetracyclines, cannabidiol, curcumin, simvastatin, atorvastatin, pravastatin, fluvastatin, rosuvastatin, pitavastatin, apigenin, telmisartan, medium and long chain fatty acids, indirubin, pregabalin, baclofen, arbaclofen, memantine, ethchlorvynol, fenobam, riluzole, gaboxadol, progabide, tulrampator, ketamine, decanoic acid, piracetam, pramiracetam and dexmethylphenidate. Most preferably, it is selected from minocycline, doxycycline, lovastatin, metformin, epigallo catechin gallate (EGCG-green tea extract), lithium, tideglusib, lamotrigine, acamprosate, ganaxolone, basimglurant, mavoglurant, methylphenidate, L-carnitine, L-acetyl carnitine. The above compounds are known from off-label use or clinical trials for treatment of symptoms fragile x syndrome. These drugs have been identified as showing synergistic effects in the treatment of fragile x syndrome, when used in combination with sulindac, based on in silico data generated from proprietary algorithms.

In a preferred embodiment, for the kits or compositions according to the present invention, Compound A is selected from the following list: zardaverine, ibudilast, metoprolol, penbutolol, fasudil, crisaborole, S-rolipram, apremilast, cilomilast, roflumilast, dipyridamole, drotaverine, propentofylline, caffeine, papaverine, trapidil, flavoxate, amlexanox, pentoxifylline, propranolol, pindolol, acebutalol, bisoprolol, carvedilol, labetalol, metipranolol, oxprenalol, pindolol, tertatolol, timolol, topirimate, tianeptine, quercetin, disulfiram, imatinib, gefitinib, selumetinib, refametinib, oglemilast and fusidic acid. Most preferably, it is selected from zardaverine, ibudilast, metoprolol, penbutolol and fasudil. These compounds have been identified as showing synergistic effects in the treatment of fragile x syndrome, when used in combination with sulindac, based on in silico data.

In a preferred embodiment, for the kits or compositions according to the present invention, Compound A is selected from the following list: carbamazepine, carnosol, riluzole, luteolin, carnosic acid, resveratrol, methylphenidate, menadione, taurine, niacin, clorazepic acid, chlordiazepoxide, diazepam and other 'azepam' class drugs. Most preferably, it is carbamazepine. These compounds have been identified as showing synergistic effects in the treatment of fragile x syndrome, when used in combination with sulindac, based on in silico data.

In a preferred embodiment, for the kits or compositions according to the present invention, Compound A is selected from midostaurin, ruxolitinib, momelotinib, bortezomib and carfilzomib; most preferably, midostaurin. These compounds have been identified in clinical trials for treatment of fragile x syndrome, but have not yet been approved. They have also been identified as showing synergistic effects in the treatment of fragile x syndrome, when used in combination with sulindac, based on in silico data.

In a preferred embodiment, for the kits or compositions according to the present invention, Compound A is selected from sildenafil, tadalafil, vardenafil, udenafil and avanafil; most preferably sildenafil and tadalafil. These compounds act through similar mechanisms to sulindac. They have also been identified as showing synergistic effects in the treatment of fragile x syndrome, when used in combination with sulindac, based on in silico data.

In a preferred embodiment, for the kits or compositions according to the present invention, Compound A is selected from gabapentin, stiripentol, ganaxolone, cannabidiol, lorazepam, phenobarbital, levetiracetam and vigabatrin; most preferably gabapentin, stiripentol and ganaxolone. These drugs are known to have anti-epileptic actions. They have also been identified as showing synergistic effects in the treatment of fragile x syndrome, when used in combination with sulindac, based on in silico data.

In a preferred embodiment, for the kits or compositions according to the present invention, Compound A is selected from fenobam, staurosporin, midostaurin, taurine, luteolin, memantine and donepezil. These drugs are known to treat memory impairment. They have also been identified as showing synergistic effects in the treatment of fragile x syndrome, when used in combination with sulindac, based on in silico data.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

The kits or compositions according to the present invention may be administered in a variety of dosage forms. In one embodiment, it may be formulated in a format suitable for oral, rectal, parenteral, intranasal or transdermal administration or administration by inhalation or by suppository.

The kits or compositions according to the present invention may be administered orally, for example as tablets, troches, lozenges, aqueous or oily suspensions, dispersible powders or granules. Preferably, the kits or compositions are formulated such that they are suitable for oral administration, for example tablets and capsules.

The kits or compositions according to the present invention may also be administered parenterally, whether subcutaneously, intravenously, intramuscularly, intrasternally, transdermally or by infusion techniques. It may also be administered as suppositories.

The kits or compositions according to the present invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed.

The present invention also provides an inhalation device containing the kits or compositions according to the present invention. Typically said device is a metered dose inhaler (MDI), which contains a pharmaceutically acceptable chemical propellant to push the medication out of the inhaler.

The kits or compositions according to the present invention may also be administered by intranasal administration. The nasal cavity's highly permeable tissue is very receptive to medication and absorbs it quickly and efficiently. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing the kits or compositions according to the present invention.

The kits or compositions according to the present invention may also be administered by transdermal administration. For topical delivery, transdermal and transmucosal patches, creams, ointments, jellies, solutions or suspensions may be employed. The present invention therefore also provides a transdermal patch containing the kits or compositions according to the present invention.

The kits or compositions according to the present invention may also be administered by sublingual administration. The present invention therefore also provides a sub-lingual tablet comprising the kits or compositions according to the present invention.

The kits or compositions according to the present invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

In an embodiment of the invention, the kits or compositions according to the present invention are administered in an effective amount to treat the symptoms of fragile x syndrome. An effective dose will be apparent to one skilled in the art, and is dependent on a number of factors such as age, sex, weight, which the medical practitioner will be capable of determining.

In a preferred embodiment, the at least one dose of sulindac comprises 5 mg to 400 mg, more preferably 50 mg to 300 mg, most preferably 150 mg to 200 mg. The lower limit for the at least one dose of sulindac is preferably 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg or 200 mg. The upper limit for a dose is preferably 400 mg, 390 mg, 380 mg, 370 mg, 360 mg, 350 mg, 340 mg, 330, mg, 320 mg, 310 mg, 300 mg, 290 mg, 280 mg, 270 mg, 260 mg, 250 mg, 240 mg, 230 mg, 220 mg or 210 mg. Any of the aforementioned lower or upper limits of the ranges may be combined with each other, and are herein disclosed. Any of the above doses may be administered once a day, twice a day, three times a day or four times a day.

In the kits or compositions according to the present invention, any of the aforementioned unit doses of sulindac may be combined with any of the aforementioned unit does of Compound A.

The kit according to the present invention provides for the administration of more than one drug, and they can be administered simultaneous, sequentially or separately. It is not necessary that they are packed together (but this is one embodiment of the invention). It is also not necessary that they are administered at the same time. As used herein, "separate" administration means that the drugs are administered as part of the same overall dosage regimen (which could comprise a number of days), but preferably on the same day. As used herein "simultaneously" means that the drugs are to be taken together or formulated as a single composition. As used herein, "sequentially" means that the drugs are administered at about the same time, and preferably within about 1 hour of each other. Preferably, the kit is administered simultaneously i.e. taken together or formulated as a single composition. Most preferably, it is formulated as a single composition.

In an embodiment of the invention, the kit is administered at least once a day. Preferably it is administered as a single daily dose. Preferably the single daily dose is administered simultaneously i.e. sulindac and Compound A are taken together or formulated as a single composition. In this embodiment, most preferably, it is formulated as a single composition. Preferably the single daily dose comprises of 200 mg to 400 mg of sulindac, preferably 300 mg to 400 mg. Preferably it comprises 200 mg, 250 mg, 300 mg, 350 mg or 400 mg of sulindac. It may also be administered sequentially i.e. at about the same time, and preferably within about 1 hour of each other.

In an embodiment of the invention, the kit may be administered twice daily. Preferably each daily dose is administered simultaneously i.e. sulindac and Compound A are taken together or formulated as a single composition. In this embodiment, most preferably, it is formulated as a single composition, which is administered twice daily. Preferably each dose comprises 150 mg to 200 mg of sulindac, with a total daily dosage of sulindac of 300 mg to 400 mg. Most preferably, each daily dose comprises 200 mg of sulindac, with a total daily dosage of sulindac of 400 mg. Each daily dose may also be administered sequentially i.e. sulindac and Compound A are administered at about the same time, and preferably within about 1 hour of each other.

In an embodiment of the invention, the kit may be administered three times per day. Preferably each daily dose is administered simultaneously i.e. sulindac and Compound A are taken together or formulated as a single composition. In this embodiment, most preferably, it is formulated as a single composition, which is administered three times daily. Preferably each dose comprises 100 mg to 130 mg of sulindac. Each daily dose may also be administered sequentially i.e. at about the same time, and preferably within about 1 hour of each other.

In an embodiment of the invention, the kit may be administered four times per day. Preferably each daily dose is administered simultaneously i.e. sulindac and Compound A are taken together or formulated as a single composition. In this embodiment, most preferably, it is formulated as a single composition, which is administered four times daily. Preferably each dose comprises 75 mg to 100 mg of sulindac. Each daily dose may also be administered sequentially i.e. at about the same time, and preferably within about 1 hour of each other.

In an embodiment of the invention, the composition is administered at least once a day. Preferably it is administered as a single daily dose. Preferably the single daily dose comprises of 200 mg to 400 mg of sulindac, preferably 300 mg to 400 mg. Preferably it comprises 200 mg, 250 mg, 300 mg, 350 mg or 400 mg.

Alternatively, the composition may be administered twice daily. Preferably each dose comprises 150 mg to 200 mg of sulindac, with a total daily dosage of sulindac of 300 mg to 400 mg. Preferably it comprises 150 mg or 200 mg. Most preferably, each daily dose comprises 200 mg of sulindac, with a total daily dosage of sulindac of 400 mg.

Alternatively, the composition may be administered three daily. Preferably each dose comprises 100 mg to 130 mg of sulindac.

Alternatively, the composition may be administered four times daily. Preferably each dose comprises 75 mg to 100 mg of sulindac.

Preferably, the dosage regime is such that the total daily dose of sulindac does not exceed 400 mg. Preferably the total daily dose of Compound A does not exceed the maximum daily dose recommended by the manufacturer. In order to treat fragile x syndrome, the kits and/or compositions are used in a chronic dosage regime i.e. chronic, long-term treatment.

The present invention also relates to a kit or composition as described herein for the manufacture of a medicament for use in the treatment of fragile x syndrome. This embodiment of the invention may have any of the preferred features described above.

The present invention also relates to a method of treating fragile x syndrome comprising administering the patient with a kit or composition as described herein. This embodiment of the invention may have any of the preferred features described above. The method of administration may be according to any of the routes described above.

The present invention also relates to use of sulindac, or a pharmaceutically acceptable salt thereof, for the manufacture of a medicament for the treatment of a patient with fragile x syndrome, wherein the patient has been administered with Compound A or a pharmaceutically acceptable salt thereof. This embodiment of the invention may have any of the preferred features described above.

The present invention also relates to use of Compound A, or a pharmaceutically acceptable salt thereof, for the manufacture of a medicament for the treatment of a patient with fragile x syndrome, wherein the patient has been administered with sulindac or a pharmaceutically acceptable salt thereof. This embodiment of the invention may have any of the preferred features described above.

The present invention also relates to use of sulindac, or a pharmaceutically acceptable salt thereof, and Compound A, or a pharmaceutically acceptable salt thereof, for the manufacture of a medicament for the treatment of fragile x syndrome. This embodiment of the invention may have any of the preferred features described above.

For the avoidance of doubt, the present invention also embraces prodrugs which react in vivo to give a compound of the present invention.

The following study illustrates the invention.

Study 1

Animals

Fmr1 knockout 2 (Fmr1 KO2) mice were generated by deletion of the promoter and first exon of Fmr1 (Mientjes et al., 2006). The Fmr1 KO2 it is both, protein and mRNA null. In this study we used Fmr1 KO2 and wild-type (WT) littermates generated on a C57BL/6J background and repeatedly backcrossed onto a C57BL/6J background for more than eight generations.

Animal Housing

The Fmr1 KO2 mice were housed in 4-5 per cage groups of the same genotype in a temperature-($21\pm1°$ C.) and humidity-controlled room with a 12-hr light-dark cycle (lights on 7 a.m.-7 p.m.). Food and water were available ad libitum. Mice were housed in commercial plastic cages, and experiments were conducted in accordance with the requirements of the UK Animals (Scientific Procedures) Act, 1986. Protocols were reviewed and approved by the IEB, University of Chile Institute review board. All experiments were conducted with the FRAXA-DVI staff blinded to genotype and drug treatment. Separate investigators prepared and coded the dosing solutions, allocated the mice to the study treatment groups, dosed the animals, and collected the behavioral data.

Treatment Groups

There were four treatment groups per compound/compound combination in the study with 10 male mice used per treatment group (all at 8 weeks of age): Group 1: Fmr1 KO2 mice treated with vehicle (Fmr1 KO2-V), Group 2: wild-type littermate mice treated with vehicle (WT-V), Group 3: Fmr1 KO2 mice treated with compounds (Fmr1 KO—[name of drug(s)]) and Group 4: wild-type littermate mice treated with compounds (WT—[name of drug(s)]).

Compound Information

Sulindac was purchased from Sigma Aldrich. Synonym: (Z)-5-Fluoro-2-methyl-1-[p-(methylsulfinyl)benzylidene]indene-3-acetic acid Metoprolol was purchased from Sigma Aldrich. Synonym: (±)-Metoprolol (+)-tartrate salt, (±) 1-(Isopropylamino)-3-[p-(β-methoxyethyl) phenoxy]-2-propanol (+)-tartrate salt, Lopressor Dosing

FIG. 1A-FIG. 1D:

Sulindac: 5 mg/kg by osmotic minipumps (ALZET Osmotic Pumps Cupertino, Calif., USA) implanted subcutaneously for 15 days delivery.

FIG. 2A-FIG. 2D:

Metoprolol: 10 mg/kg by osmotic minipumps implanted subcutaneously for 15 days.

FIG. 3A-FIG. 3D:

Sulindac: 5 mg/kg by osmotic minipumps implanted subcutaneously for 15 days. Ibudilast: 3 mg/kg by osmotic minipumps implanted subcutaneously for 15 days. KO+Sul/Ibu: 5 mg/kg of sulindac and 3 mg/kg of ibudilast by osmotic minipumps implanted subcutaneously for 15 days.

FIG. 4A-FIG. 4D:

Sulindac: 5 mg/kg by osmotic minipumps implanted subcutaneously for 15 days. Sertraline: 1 mg/kg by osmotic minipumps implanted subcutaneously for 15 days. KO+Sul/Ser: 5 mg/kg of sulindac and 1 mg/kg of sertraline by osmotic minipumps implanted subcutaneously for 15 days.

FIG. 5A-FIG. 5E:

Sulindac: 5 mg/kg by osmotic minipumps implanted subcutaneously for 15 days. Quercetin: 1 mg/kg by osmotic minipumps implanted subcutaneously for 15 days. KO+Sul/Quer: 5 mg/kg of sulindac and 100 mg/kg of quercetin by osmotic minipumps implanted subcutaneously for 15 days.

FIG. 6A-FIG. 6D:

Sulindac: 5 mg/kg by osmotic minipumps implanted subcutaneously for 15 days. Cannabidiol: 5 mg/kg by osmotic minipumps implanted subcutaneously for 15 days. KO+Sul/CBD: 5 mg/kg of sulindac and 5 mg/kg of cannabidiol by osmotic minipumps implanted subcutaneously for 15 days.

FIG. 7A-FIG. 7D:

Sulindac: 5 mg/kg by osmotic minipumps implanted subcutaneously for 15 days. Minocycline: 30 mg/kg by osmotic minipumps implanted subcutaneously for 15 days.

KO+Sul/Min: 5 mg/kg of sulindac and 30 mg/kg of minocycline by osmotic minipumps implanted subcutaneously for 15 days.

FIG. 8A-FIG. 8E:

Sulindac: 5 mg/kg by osmotic minipumps implanted subcutaneously for 15 days. KO+S+T 5 mg/kg of sulindac and 47 mg/kg of topiramate by osmotic minipumps implanted subcutaneously for 15 days.

Behavioral Testing

For experiments, all mice were tested once in the same apparatus. Prior to testing, mice were placed in the apparatus for some minutes before the experiment. The apparatus was cleaned with moist and dry tissues before testing each mouse. The aim was to create a low but constant background mouse odor for all experimental subjects. Testers were blind to the genotype and treatment during all testing and data analysis. We assessed weight loss, fur loss, walking, eyes open, eye discharges and general behavior. All signs indicated that all treatments were well tolerated by the Fmr1KO2 mice and WT littermates at all times.

Open Field

The open-field apparatus was used to test hyperactivity. The apparatus was a gray PVC-enclosed arena 50×9×30 cm divided into a 10×10 cm grid. Mice were brought to the experimental room 5-20 min before testing. A mouse was placed into a corner square facing the corner and observed for 3 min. The number of squares entered by the whole body (locomotor activity) were counted. The movement of the mouse around the field was recorded with a video tracking device for 3 min (version NT4.0, Viewpoint).

Nesting

The test was performed in individual cages. Normal bedding covered the floor to a depth of 0.5 cm. Each cage was supplied with a "Nestlet," a 5 cm square of pressed cotton batting (Ancare). Mice were placed individually into the nesting cages 1 hr. before the dark phase, and the results were assessed the next morning. Nest building was scored on a 5 point scale.

Score 1: The Nestlet was largely untouched (>90% intact).

Score 2: The Nestlet was partially torn up (50-90% remaining intact).

Score 3: The Nestlet was mostly shredded but often there was no identifiable nest site: <50% of the Nestlet Score 4: An identifiable, but flat nest <90% of the Nestlet was torn up, the material was gathered into a flat nest with walls higher than the mouse height curled up on its side) on less than 50% of its circumference.

Score 5: A (near) perfect nest: >90% of the Nestlet was torn up, the nest was a crater, with walls higher than mouse body height on more than 50% of its circumference.

Fear Conditioning

The dependent measure used in contextual fear conditioning was a freezing response following a pairing of an unconditioned stimulus (foot shock), with a conditioned stimulus, a particular context. Freezing is a species-specific response to fear, which has been defined as "absence of movement except for respiration". This may last for seconds to minutes depending on the strength of the aversive stimulus, the number of presentations, and the degree of learning achieved by the subject. Testing involved placing the animal in a novel environment (dark chamber), providing an aversive stimulus (a 1-sec electric shock, 0.2 mA, to the paws), and then removing it.

Social Interaction

In the three-chambered sociability task, a subject mouse was evaluated for its exploration of a novel social stimulus (novel mouse). The three-chambered social approach task monitors direct social approach behaviors when a subject mouse is presented with the choice of spending time with either a novel mouse or an empty cup. Sociability is defined as the subject mouse spending more time in the chamber containing the mouse than in the empty chamber. Preference for social novelty is defined as spending more time in the chamber with the novel mouse. The apparatus is a rectangular three-chamber box, where each chamber measures 20 cm (length)×40.5 cm (width)×22 cm (height). Dividing walls are made from clear perplex, with small openings (10 cm width×5 cm height) that allow access into each chamber. The three chamber task was lit from below (10 lux). The mice were allowed to freely explore the three-chamber apparatus over three 10 min trials. During the trial one wire cup was placed upside down in one of the side chambers and a novel mouse was placed under another wire cup in the other side chamber (novel mouse stimulus), leaving the middle chamber empty. The location of the novel mouse across trials was counterbalanced to minimize any potential confound due to a preference for chamber location. The time spent exploring the novel mice was scored as exploration ratio.

Stereotypy

Rates of spontaneous stereotypy (head movements) were assessed using a modified automated photocell detection apparatus obtained from Columbus Instruments (Columbus, Ohio). The testing protocol involved removing mice from their home cages and placing them singly in testing cages (22×25×28 cm) made of Plexiglas. The mice were left undisturbed for 2 for habituation and recovery from the stress of handling prior to the beginning of the testing. Food and water were provided. Each animal received a stereotypy score that represented the average stereotypy frequency per hour.

Self-Grooming

Each mouse was placed individually into a standard mouse cage, (46 cm length×23.5 cm wide×20 cm high), illuminated at −40 lux. After a 5-min habituation period in the test cage, each mouse was scored in seconds for cumulative time spent grooming all body regions.

Hyponeophagia

Mice are cautious when presented with a novel food in a novel place and this is reflected in the latency to eat; the more anxious the animal, the longer the latency. To assist in test standardization (between group and singly housed animals) the mice are put into new individual temporary holding cages and allowed 20 min in the new cage in the test room to adapt. Individual housing also prevents social transmission of food preferences. Full cream sweetened condensed milk diluted 50:50 with water is used as the novel food. Mice are food restricted overnight: remove all food the evening before (also put down clean new bedding as they're coprophagic) then give 1 g/mouse, which is approximately a third of what they would normally eat. If they are group housed make sure that the pieces are small so that all mice get equal shares. Test them the next morning and replace their food as soon as testing is finished. The apparatus is a white perspex base (30 cm$^2$) to which is glued a food well 1.2 cm in diameter, 0.9 cm high, filled with milk. To contain the mouse on the base and facilitate investigation of the milk, a translucent plastic jug (approximate volume 1.5 l, 15 cm diameter with a spout protruding a further 2 cm) is placed upside down with the spout forming a small alcove over the food well. This focuses the attention of the mouse on to the well and the milk, so minimizing the effects of treatments that might affect perception of, or orientation to, the food source. The mouse is placed facing away from the well and the jug is gently lowered into position, taking care not to trap the tail. The latency from being placed in the apparatus to start properly drinking is taken. Sniffs at the milk do not count, at least two seconds of lapping should occur. Count any faecal boli and note any urination (note that these measures will be influenced by the time in the apparatus). The cut-off time is 2 min. This time is probably optimal for anxiety levels to decrease while still preserving a state of habituation to the apparatus. The test parameter is the (cumulative) latency to drink. As in other tests where odor could play a significant role, non-experimental mice should be placed in the apparatus before testing starts.

Statistical Analysis of Behavioral Data

Data were analyzed by two-way analysis of variance (ANOVA) followed by post-test comparisons where appropriate using Tukey's Multiple Comparison Test. Data are represented as the mean and standard error of the mean (SEM). Statistical analyses were performed in GraphPad Prism 7.03.

Sulindac

Figure 1A:
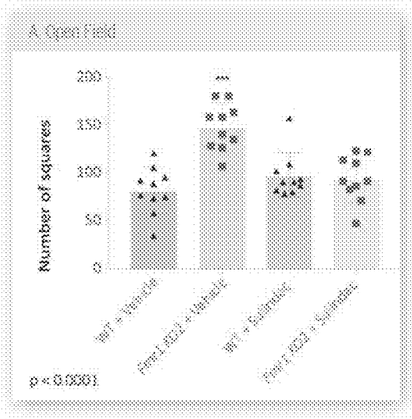
FIG. 1A-FIG. 1D show the results from sulindac in vivo testing.

The results can be seen in FIG. 1A-FIG. 1D:

A. Fifteen-day chronic treatment with sulindac normalizes hyperactivity displayed by the Fmr1 KO2 mice.

Figure 1B:
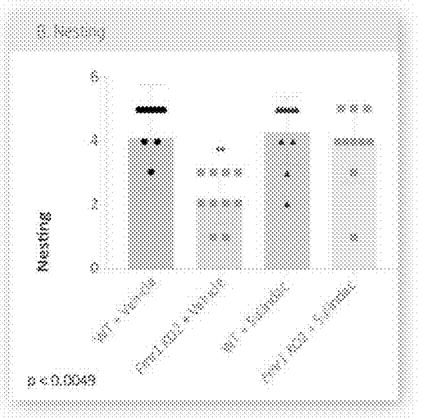

B. Fmr1 KO2 mice treated with sulindac showed normalization in nesting behavior.

Figure 1C:
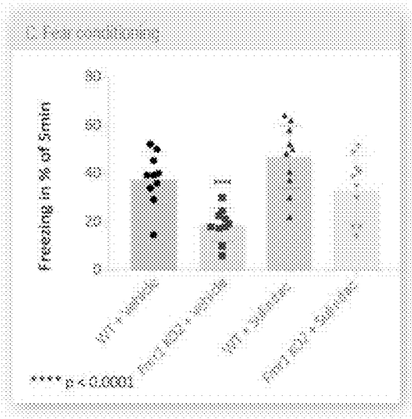

C. In the contextual memory test, freezing was reduced in Fmr1 KO2 mice when compared to freezing of WT littermates. Treatment with Sulindac ameliorates the Fmr1 KO deficit in learning and memory (KO not different from WT, p=0.3968).

Figure 1D:
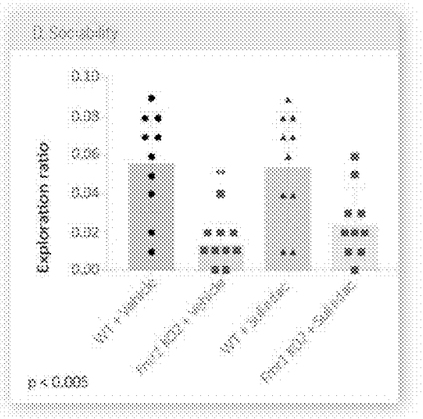

D. Fmr1 KO2 mice showed a significantly lower exploration index of the novel mouse compared to WT mice ($p<0.005$), indicating impaired sociability. Sulindac partially improved such impairment in Fmr1 KO2 mice.

Metoprolol

The results can be seen in FIG. 2A-FIG. 2D.

Figure 2A:
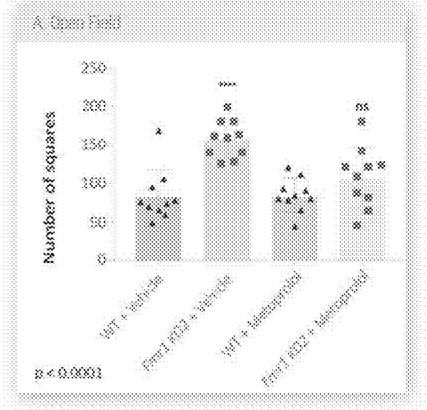
FIG. 2A-FIG. 2D show the results from metoprolol in vivo testing.

A. Chronic treatment with metoprolol normalized Fmr1 KO2 mice hyperactivity as total distance travelled in the open field ($p<0.005$)

Figure 2B:
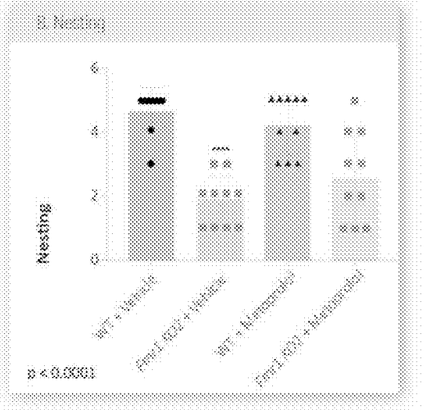

B. Nesting is partially rescued in the Fmr1 KO2 after metoprolol treatment.

Figure 2C:
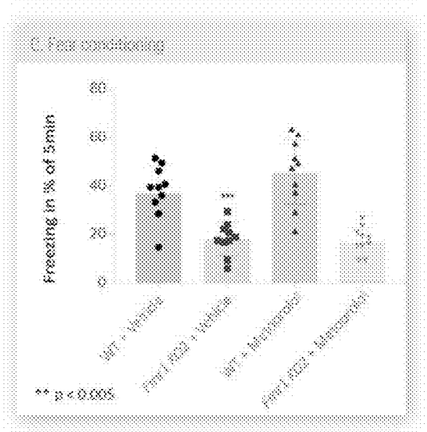

C. The absence of FMRP protein impairs contextual fear conditioning; chronic treatment with metoprolol fails to improve the learning deficits observed in the Fmr1 KO2 mouse.

Figure 2D:
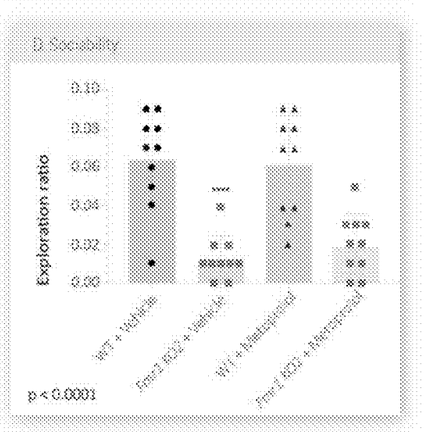
Figure 3A:
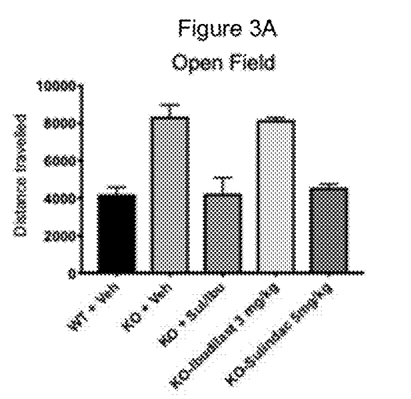
FIG. 3A-FIG. 3D show the results from sulindac and ibudilast in vivo testing.
Figure 3B:
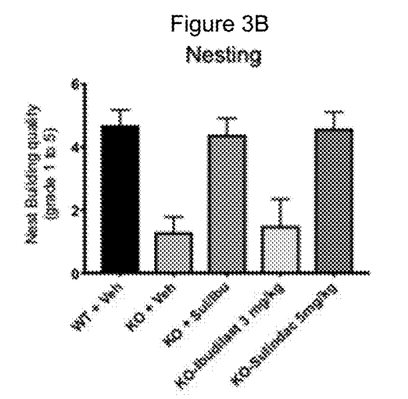
Figure 3C:
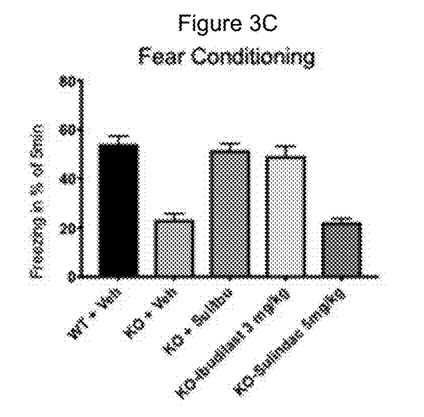
Figure 3D:
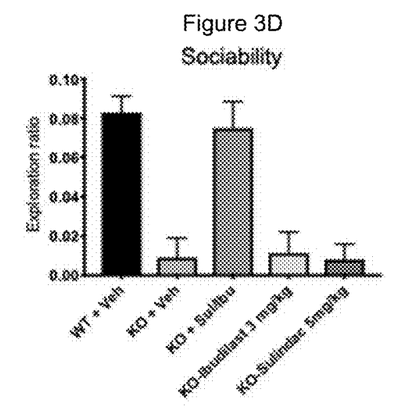
Figures 4A, 4B:
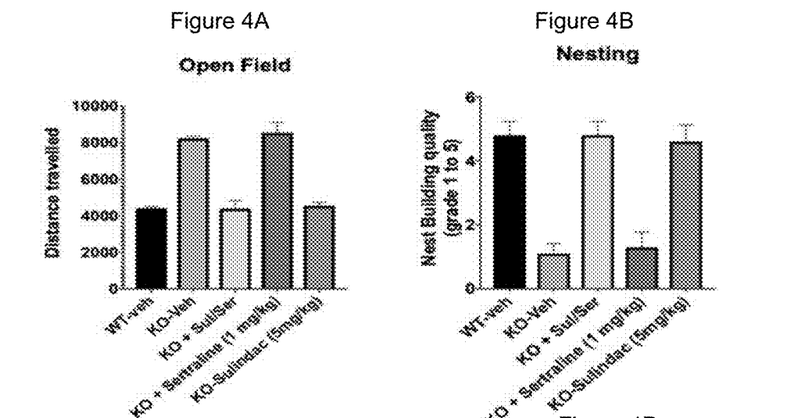
FIG. 4A-FIG. 4D show the results from sulindac and sertraline in vivo testing.
Figure 4C:
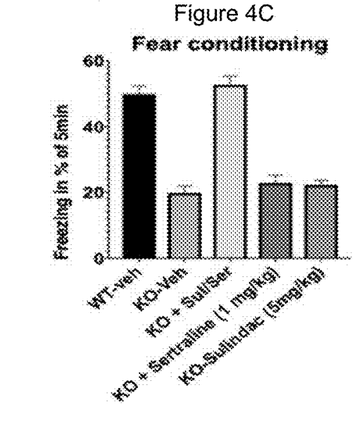
Figure 4D:
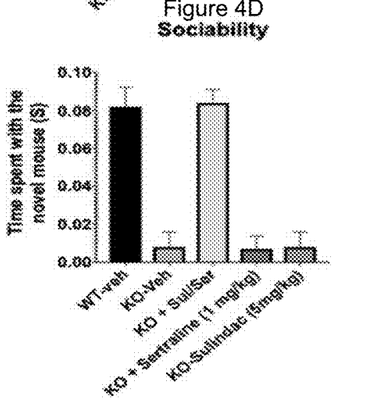
Figure 5A:
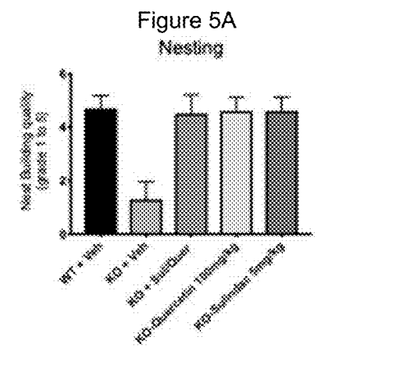
FIG. 5A-FIG. 5E show the results from sulindac and quercetin in vivo testing.
Figure 5B:
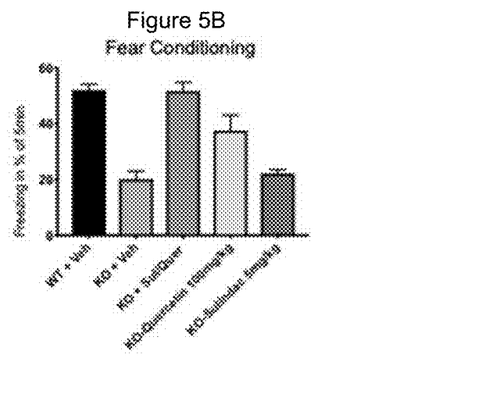
Figure 5C:
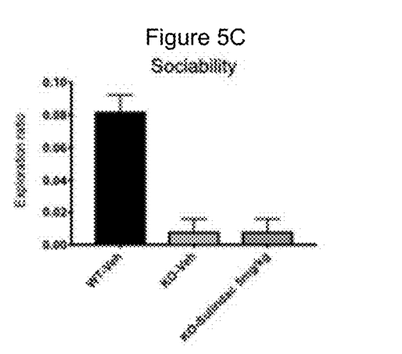
Figure 5D:
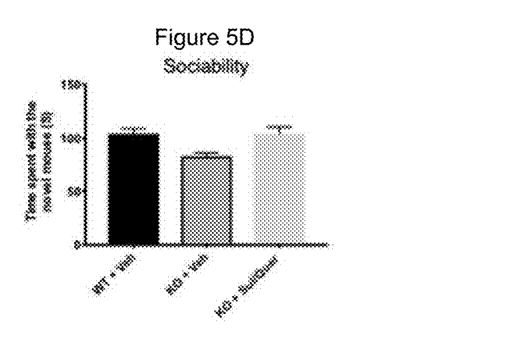
Figure 5E:
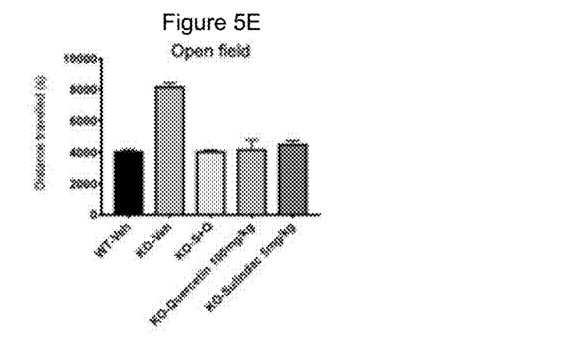
Figure 6A:
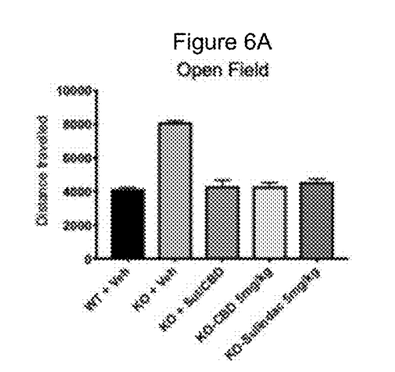
FIG. 6A-FIG. 6D show the results from sulindac and cannabidiol in vivo testing.
Figure 6B:
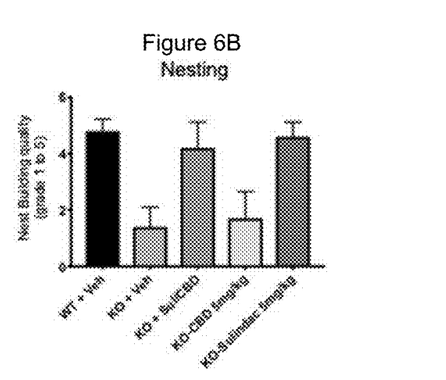
Figure 6C:
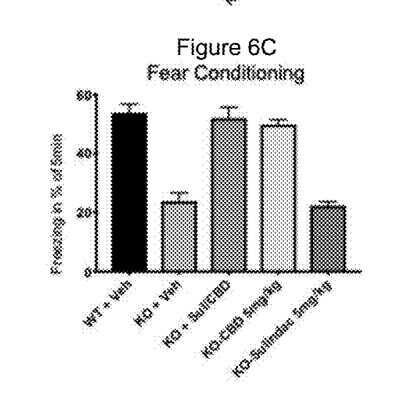
Figure 6D:
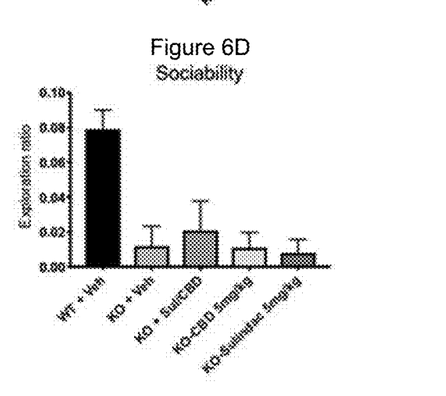
Figure 7A:
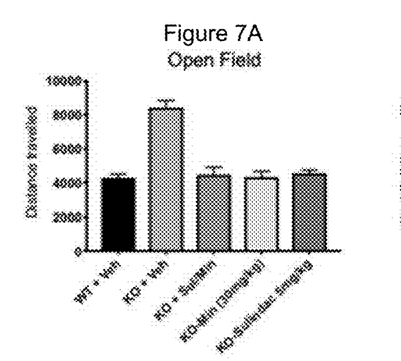
FIG. 7A-FIG. 7D show the results from sulindac and minocycline in vivo testing.
Figure 7B:
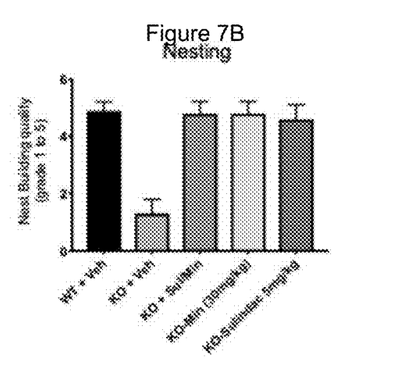
Figure 7C:
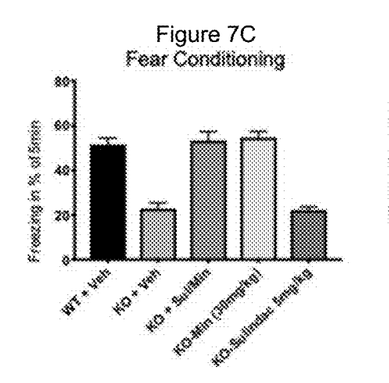
Figure 7D:
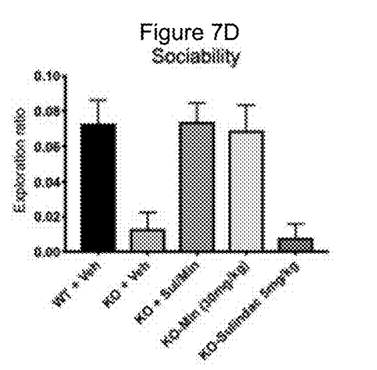
Figure 8A:
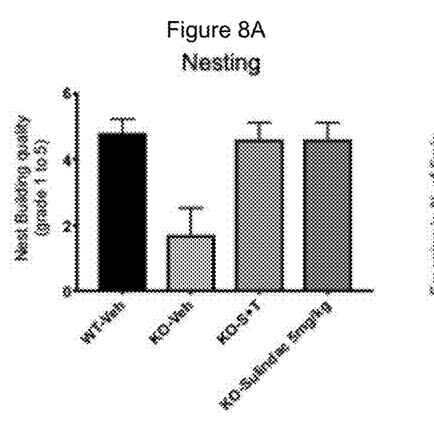
FIG. 8A-FIG. 8E show the results from sulindac and topiramate in vivo testing.
Figure 8B:
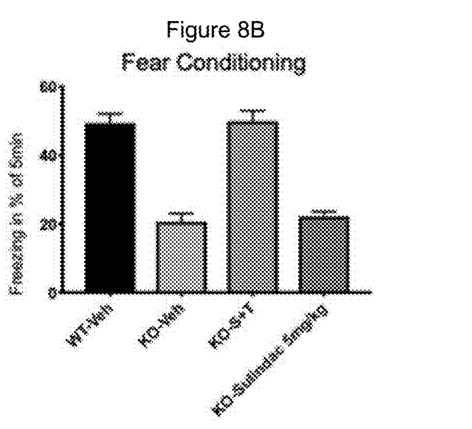
Figure 8C:
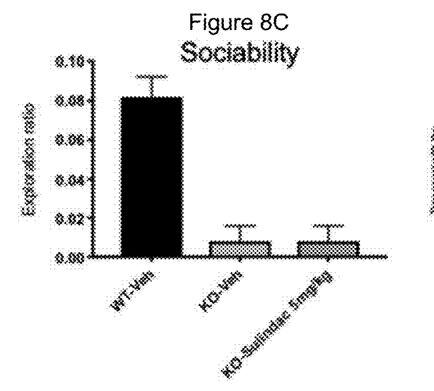
Figure 8D:
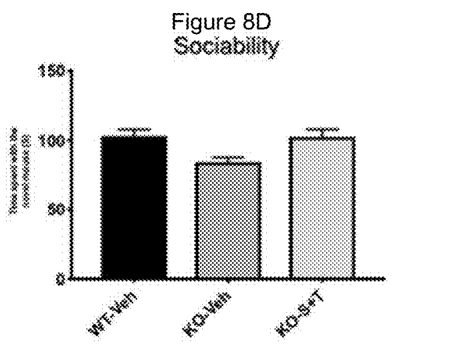
Figure 8E:
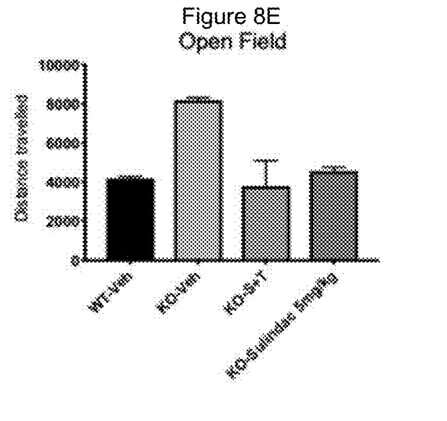

D. No significant difference was found in sociability in Fmr1 KO2 mice treated with metoprolol compared to drug treated WT mice ($p<0.0001$).

As seen in FIG. 1A-FIG. 1D, Chronic treatment with sulindac significantly improved the Fmr1 KO2 mouse phenotype, fully rescuing open field and nesting behavior, while partially rescuing contextual fear conditioning and sociability. As can be seen from FIG. 2A-FIG. 2D, chronically administering metoprolol was able to normalize hyperactivity and partially rescue nesting behavior and sociability. This is evidence that sulindac and metoprolol are useful in the therapy of fragile x syndrome.

Sulindac and Ibudilast

As can be seen from FIG. 3A-FIG. 3D, the combination of sulindac and ibudilast rescued sociability without affecting other behavioral tests. A synergistic effect is seen as, at the dosage amounts used, neither sulindac nor ibudilast alone rescues sociability. Open field, fear conditioning and nesting are rescued by ibudilast in combination with sulindac, showing no interference. This is evidence that the combination of sulindac and ibudilast is useful in the treatment of FXS, and shows synergistic effects.

Sulindac and Sertraline

As can be seen from FIG. 4A-FIG. 4D, the combination of sulindac and sertraline rescued fear conditioning and sociability without affecting other behavioral tests. A synergistic effect is seen as, at the dosage amounts used, neither sulindac nor sertraline alone rescues sociability or fear conditioning. Open field and nesting are rescued by sertraline in combination with sulindac, showing no interference. This is evidence that the combination of sulindac and sertraline is useful in the treatment of FXS, and shows synergistic effects.

Sulindac and Quercetin

As can be seen from FIG. 5A-FIG. 5E, the combination of sulindac and quercetin rescued fear conditioning without affecting other behavioral tests. A synergistic effect is seen as, at the dosage amounts used, neither sulindac nor quercetin alone fully rescues fear conditioning. Nesting and open field are rescued by sulindac and quercetin in combination, showing no interference. The combination of sulindac and quercetin rescued sociability. This is evidence that the combination of sulindac and quercetin is useful in the treatment of FXS, and shows synergistic effects.

Sulindac and Cannabidiol

As can be seen from FIG. 6A-FIG. 6D, the combination of sulindac and cannabidiol fully rescued open field, nesting and fear conditioning. Sociability was slightly improved by the combination of sulindac and cannabidiol. The two drugs do not interfere with each other. This is evidence that the combination of sulindac and cannabidiol is useful in the treatment of FXS.

Sulindac and Minocycline

As can be seen from FIG. 7A-FIG. 7D, the combination of sulindac and minocycline was fully active, rescuing all behavioral tests. The two drugs do not interfere with each other. This is evidence that the combination of sulindac and minocycline is useful in the treatment of FXS.

Sulindac and Topiramate

As can be seen from FIG. 8A-FIG. 8E, the combination of sulindac and topiramate was fully active, rescuing all behavioral tests. The two drugs do not interfere with each other. This is evidence that the combination of sulindac and topiramate is useful in the treatment of FXS.

The invention claimed is:

1. A method of treating fragile x syndrome by combination therapy in a subject in need thereof comprising administering to the subject simultaneously, separately or sequentially an effective amount of the combination of:
   (i) sulindac, or a pharmaceutically acceptable salt thereof; and
   (ii) sertraline or a pharmaceutically acceptable salt thereof.

2. The method of claim 1, wherein the subject exhibits signs of hyperactivity, social anxiety, memory loss, or disruptive behaviour.

3. The method of claim 1, wherein the subject is human.

4. The method of claim 1, wherein sulindac and sertraline are administered simultaneously in a single dose once per day.

5. The method of claim 4, wherein the single dose comprises 200 mg to 400 mg of sulindac.

6. The method of claim 1, wherein sulindac and sertraline are administered simultaneously in a single dose twice per day.

7. The method of claim 6, wherein the single dose comprises 150 mg to 200 mg of sulindac.

8. The method of claim 1, wherein sulindac and sertraline are administered orally.

9. The method of claim 1, wherein sulindac and sertraline are administered parenterally, transdermally, sublingually, rectally or by inhalation.

10. The method of claim 1, wherein the subject is human; and sulindac and sertraline are administered simultaneously in a single dose once per day.

11. The method of claim 1, wherein the subject is human; and sulindac and sertraline are administered simultaneously in a single dose twice per day.

* * * * *